US010894750B2

(12) United States Patent
Vecchini et al.

(10) Patent No.: US 10,894,750 B2
(45) Date of Patent: Jan. 19, 2021

(54) PROCESS FOR THE DEHYDRATION OF OXYGENATED COMPOUNDS

(71) Applicant: versalis S.p.A., San Donato Milanese (IT)

(72) Inventors: Nicola Vecchini, Verona (IT); Gianni Girotti, San Giuliano Milanese (IT)

(73) Assignee: versalis S.p.A., San Donato Milanese (IT)

(*) Notice: Subject to any disclaimer, the term of this patent is extended or adjusted under 35 U.S.C. 154(b) by 0 days.

(21) Appl. No.: 15/540,399

(22) PCT Filed: Feb. 22, 2016

(86) PCT No.: PCT/IB2016/050926
§ 371 (c)(1),
(2) Date: Jun. 28, 2017

(87) PCT Pub. No.: WO2016/135605
PCT Pub. Date: Sep. 1, 2016

(65) Prior Publication Data
US 2018/0002249 A1  Jan. 4, 2018

(30) Foreign Application Priority Data

Feb. 23, 2015  (IT) .............................. MI2015A0261

(51) Int. Cl.
| *C07C 1/24* | (2006.01) |
| *B01J 23/10* | (2006.01) |
| *C07C 29/60* | (2006.01) |
| *B01J 37/03* | (2006.01) |
| *C07C 11/167* | (2006.01) |
| *B01J 21/12* | (2006.01) |
| *B01J 35/02* | (2006.01) |

(52) U.S. Cl.
CPC ................ *C07C 1/24* (2013.01); *B01J 21/12* (2013.01); *B01J 23/10* (2013.01); *B01J 37/031* (2013.01); *C07C 11/167* (2013.01); *C07C 29/60* (2013.01); *B01J 35/023* (2013.01); *C07C 2521/08* (2013.01); *C07C 2521/12* (2013.01)

(58) Field of Classification Search
CPC ....................................................... C07C 1/20
See application file for complete search history.

(56) References Cited

U.S. PATENT DOCUMENTS

| 2,373,153 | A | * | 4/1945 | Tollefson | .................. | C07C 1/24 |
| | | | | | | 585/611 |
| 3,600,455 | A | | 8/1971 | Dean | | |
| 3,979,336 | A | | 9/1976 | Golosman et al. | | |
| 6,797,851 | B2 | * | 9/2004 | Martens | .................... | C07C 1/20 |
| | | | | | | 585/639 |
| 7,442,845 | B2 | * | 10/2008 | Gao | .......................... | C07C 1/20 |
| | | | | | | 502/355 |
| 2003/0065233 | A1 | * | 4/2003 | Fuji | ............................ | C07C 1/20 |
| | | | | | | 585/639 |
| 2003/0078463 | A1 | | 4/2003 | Martens et al. | | |
| 2007/0100186 | A1 | | 5/2007 | Gao et al. | | |
| 2008/0058572 | A1 | * | 3/2008 | Fernandez | ............... | C07C 1/24 |
| | | | | | | 585/640 |
| 2008/0103345 | A1 | * | 5/2008 | Levin | ....................... | C07C 1/20 |
| | | | | | | 585/640 |
| 2009/0178955 | A1 | * | 7/2009 | Ryu | ........................ | B01J 21/12 |
| | | | | | | 208/120.01 |
| 2009/0270668 | A1 | * | 10/2009 | Bailey | ....................... | C07C 1/24 |
| | | | | | | 585/639 |
| 2011/0313213 | A1 | * | 12/2011 | Minoux | .................... | C07C 1/24 |
| | | | | | | 568/916 |

(Continued)

FOREIGN PATENT DOCUMENTS

| CN | 1397536 A | 2/2003 |
| CN | 101172920 A | 5/2008 |

(Continued)

OTHER PUBLICATIONS

Sato et al. Selective dehydration of diols to allylic alcohols catalyzed by ceria, 2003, vol. 4, 77-81 (Year: 2003).*
Ray. Guayule: A Source of Natural Rubber. 1993, New Crops p. 338-343, Wiley New York (Year: 1993).*
International Search Report and Written Opinion dated Apr. 25, 2016 in PCT/IB2016/050926.
V. K. Diez, et al., "Gas-phase conversion of 1,3-butanediol on single acid-base and Cu-promoted oxides", Catalysis Today, vol. 213, XP028674832, Apr. 18, 2013, pp. 18-24.
Combined Chinese Office Action and Search Report dated Aug. 27, 2019, in Patent Application No. 201680005528.5, citing documents AA, AO and AX therein, 30 pages (with unedited computer generated English translation).
Ichikawa, N. et al., "Catalytic reaction of 1,3-butanediol over solid acids", Journal of Molecular Catalysis, vol. 256, No. 1-2, Aug. 18, 2006, pp. 106-112 (with English abstract).

(Continued)

*Primary Examiner* — In Suk C Bullock
*Assistant Examiner* — Alyssa L Cepluch
(74) *Attorney, Agent, or Firm* — Oblon, McClelland, Maier & Neustadt, L.L.P.

(57) ABSTRACT

The present invention relates to a process for the dehydration of at least one oxygenated compound, preferably selected from saturated alcohols, unsaturated alcohols, diols, ethers, in the presence of at least one dehydration catalyst selected from cerium oxide ($CeO_2$), aluminium oxide ($\gamma$-$Al_2O_3$), aluminium silicate, silica-aluminas ($SiO_2$—$Al_2O_3$), aluminas, zeolites, sulfonated resins, ion-exchange resins, metal oxides (for example, lanthanum oxide, zirconium oxide, tungsten oxide, thallium oxide, magnesium oxide, zinc oxide); of at least one basic agent selected from ammonia ($NH_3$), or from inorganic or organic compounds containing nitrogen capable of developing ammonia ($NH_3$) during said dehydration process; and, optionally, of silica ($SiO_2$), or of at least one catalyst for the dissociation of ammonia ($NH_3$) selected from catalysts comprising silica ($SiO_2$), preferably of silica ($SiO_2$).

13 Claims, No Drawings

(56) References Cited

U.S. PATENT DOCUMENTS

| | | | | |
|---|---|---|---|---|
| 2012/0101320 A1* | 4/2012 | Stewart | ............... | C07C 1/24 585/324 |
| 2013/0012748 A1* | 1/2013 | Liu | ............... | C07C 1/20 585/639 |
| 2013/0217943 A1* | 8/2013 | Minoux | ............... | C07C 1/24 585/640 |
| 2015/0218062 A1* | 8/2015 | Lilga | ............... | C07C 1/24 568/903 |
| 2015/0284307 A1 | 10/2015 | Lilga et al. | | |
| 2015/0361007 A1* | 12/2015 | Millet | ............... | C07C 319/20 526/113 |
| 2016/0184810 A1* | 6/2016 | Wright | ............... | B01J 37/0201 526/335 |

FOREIGN PATENT DOCUMENTS

| | | |
|---|---|---|
| EP | 1 277 719 A1 | 1/2003 |
| SU | 910187 | 3/1982 |
| WO | WO 2010/025241 A2 | 3/2010 |
| WO | 2011/161045 | 12/2011 |
| WO | 2013/004533 | 1/2013 |
| WO | WO-2014118484 A1 * | 8/2014 ............ C07C 1/24 |

OTHER PUBLICATIONS

Indian Examination Report dated Sep. 19, 2019, in Patent Application No. 201747032423, citing document AO therein, 5 pages.

Office Action as received in the corresponding Russian patent application No. 2017130690/04(053428) dated Feb. 27, 2109 w/English Translation (Office Action Inquiry attached).

Search Report as received in Russian Patent Application No. 2017130690/04(053428) dated Feb. 22, 2019 w/English Translation.

Combined Chinese Office Action and Search Report dated Jun. 1, 2020, in Patent Application No. 201680005528.5 (with English translation), citing document AX therein, 28 pages.

Dai Zhicheng et al, "Production and Application of Silicon Compounds" Chengdu University of Science and Technology Press, 1st Edition, May 1994, which was published on May 31, 1994, pp. 211-217 (with partial English translation).

European Office Action dated Jul. 2, 2020 in European Patent Application No. 16712502.0, citing documents AA, AB, AO and AP therein, 8 pages.

* cited by examiner

PROCESS FOR THE DEHYDRATION OF OXYGENATED COMPOUNDS

The present invention relates to a process for the dehydration of oxygenated compounds.

More specifically, the present invention relates to a process for the dehydration of at least one oxygenated compound, preferably selected from saturated alcohols, unsaturated alcohols, diols, ethers, in the presence of at least one dehydration catalyst selected from cerium oxide ($CeO_2$), aluminium oxide ($\gamma$-$Al_2O_3$), aluminium silicate, silica-aluminas ($SiO_2$—$Al_2O_3$), aluminas, zeolites, sulfonated resins, ion-exchange resins, metal oxides (for example, lanthanum oxide, zirconium oxide, tungsten oxide, thallium oxide, magnesium oxide, zinc oxide); of at least one basic agent selected from ammonia ($NH_3$), or from inorganic or organic compounds containing nitrogen capable of developing ammonia ($NH_3$) during said dehydration process; and, optionally, of silica ($SiO_2$), or of at least one catalyst for the dissociation of ammonia ($NH_3$) selected from catalysts comprising silica ($SiO_2$), preferably of silica ($SiO_2$).

The present invention also relates to a process for the dehydration of at least one oxygenated compound, preferably selected from saturated alcohols, unsaturated alcohols, diols, ethers, comprising feeding to a reactor including at least a first catalytic bed comprising silica ($SiO_2$), or at least a first catalytic bed comprising at least one catalyst for the dissociation of ammonia ($NH_3$) selected from catalysts comprising silica ($SiO_2$), preferably at least a first catalytic bed comprising silica ($SiO_2$), and at least a second catalytic bed comprising at least one dehydration catalyst selected from cerium oxide ($CeO_2$), aluminium oxide ($\gamma$-$Al_2O_3$), aluminium silicate, silica-aluminas ($SiO_2$—$Al_2O_3$), aluminas, zeolites, sulfonated resins, ion-exchange resins, metal oxides (for example, lanthanum oxide, zirconium oxide, tungsten oxide, thallium oxide, magnesium oxide, zinc oxide), a mixture comprising said at least one oxygenated compound and at least one basic agent selected from ammonia ($NH_3$), or from inorganic or organic compounds containing nitrogen capable of developing ammonia ($NH_3$) during said dehydration process, said mixture being fed to said reactor so as to pass first through said first catalytic bed and subsequently through said second catalytic bed.

The present invention also relates to a process for the dehydration of at least one oxygenated compound, preferably selected from saturated alcohols, unsaturated alcohols, diols, ethers, comprising feeding to a reactor including at least a first catalytic bed comprising silica ($SiO_2$), or at least a first catalytic bed comprising at least one catalyst for the dissociation of ammonia ($NH_3$) selected from catalysts comprising silica ($SiO_2$), preferably at least a first catalytic bed comprising silica ($SiO_2$), and at least a second catalytic bed comprising at least one dehydration catalyst selected from ammonium phosphate, or from phosphates of metals such as, for example, boron phosphate, aluminium phosphate, calcium phosphate, sodium phosphate, cerium phosphate, preferably calcium phosphate, a mixture comprising said at least one oxygenated compound and at least one basic agent selected from ammonia ($NH_3$), or from inorganic or organic compounds containing nitrogen capable of developing ammonia ($NH_3$) during said dehydration process, said mixture being fed to said reactor so as to pass first through said first catalytic bed and subsequently through said second catalytic bed.

Said saturated alcohols, unsaturated alcohols, diols, ethers, preferably derive from the fermentation of sugars obtained from biomass.

The present invention also relates to a process for the dehydration of 1,3-butanediol, said 1,3-butanediol being preferably obtained from the fermentation of sugars obtained from biomass to give unsaturated alcohols, said unsaturated alcohols being subsequently subjected to distillation and to a further dehydration process, obtaining 1,3-butadiene. Said 1,3-butadiene can be advantageously used as monomer or as intermediate in the production of elastomeric materials, thermoplastic materials, and also materials based on (co)polymers.

It is known that the dehydration of alcohols takes place through an acidic catalysis and the main product obtained is the olefin having a number of carbon atoms corresponding to the starting alcohol, or the ether of said alcohol.

In reality, together with the main reactions, secondary reactions also take place, which lead to the formation of carbonyl compounds such as, for example, aldehydes, ketones, carboxylic acids. Said carbonyl compounds can be formed thanks to the dehydrogenating component present in some dehydration catalysts such as, for example, alumina and silica-aluminas, wherein said component can be more or less marked. Other secondary reactions that can take place are the oligomerization of olefins and the "cracking" phenomena. Said secondary reactions provide compounds that act as precursors of coke and which therefore lead to a deactivation of the dehydration catalyst due to formation of coke and/or of pitch which, in a relatively short time, cover all the active surface of the catalyst used for the dehydration, making it completely inactive.

Deactivation mechanisms of catalysts are widely known in literature. Detailed descriptions of these mechanisms can be found, for example, in Petersen Z. and Bell A. T., "*Catalyst Deactivation*" (1987), Marcel Dekker, INC, N.Y.; Forzatti P. et al., "Catalyst deactivation", "*Catalysis Today*" (1999), Vol. 52, pages 165-181; Bartholomew C.H., "Mechanisms of catalyst deactivation", "*Applied Catalysis A: General*" (2001), Vol. 212, pages 17-60.

The main deactivation mechanisms of catalysts can be attributed to three fundamental categories: poisoning, formation of carbonaceous deposits or "coking", fouling of the catalyst.

The poisoning of a catalyst is generally due to the fixation of compounds on its active centres, that inhibit its activity. With respect to said poisoning, one of the methods for avoiding this phenomenon is the elimination, upstream, of the potentially poisonous compounds through techniques such as, for example, distillation, extraction, or absorption on specific materials.

With respect, on the other hand, to the formation of carbonaceous deposits ("coking") and the fouling of the catalyst, resort is very often made to oxidative regeneration, and therefore to the elimination of these deposits by combustion of the same using suitable techniques which, however, must avoid sintering phenomena of the catalyst whose activity is to be restored, or to methods that reduce the fouling process during the reaction.

As indicated above, the formation of carbonaceous deposits ("coking") is generally due to the formation of compounds, on the part of secondary reactions, which act as precursors of coke. In the article of Bartholomew C. H., "Mechanisms of catalyst deactivation", "*Applied Catalysis A: General*" (2001), Vol. 212, pages 17-60, mentioned above, the polymerization and cyclization of olefins in the presence of Brønsted acids or bases as catalysts, are indicated, inter alia, as secondary reactions that cause the formation of coke. As the catalysts used in the dehydration of alcohols mainly belong to the group of Brønsted and Lewis acids, the occurrence of these secondary reactions is considered as being extremely likely and still represents a very significant industrial problem.

Furthermore, in the case of the dehydration of alcohols, one of the problems found in literature, which leads to the deactivation of the catalyst, is the presence of carbonyl compounds in the feedstock (reaction mixture). Aldehydes, in particular, can react forming compounds precursors of coke. This is a long well-known phenomenon, as described, for example, in the letter nr. 455 of 24/9/1938 addressed by Dr. Maximoff to Prof. Natta reported in "La Gomma Artificiale—Giulio Natta e i Laboratori Pirelli" (2013), pages 132-133, edited by Redondi P., Guerrini and Associati Editors. More recent citations can be found, for example, in the article of de Klerk A., "Key catalyst types for the efficient refining of Fischer-Tropsch syncrude: alumina and phosphoric acid", "*Catalysis*" (2011), Vol. 23, pages 1-49, in which on page 17, it can be read that the deactivation of alumina-based catalysts, used in the dehydration of alcohols, is caused by the fouling of catalysts mainly due to the carbonyl compounds that can be present in the feedstock or which can be formed during the dehydration of alcohols. It is also known that dehydration catalysts such as, for example, alumina and other metal oxides, also exert a dehydrogenating action which can lead to the formation of carbonyl compounds. The above-mentioned dehydrogenation phenomenon is described, for example, on page 11 of the above article of de Klerk A., but this has also been known for some time. Sabatier P. et al. for example, in "*Annales de chimie et de physique*" (1910), Vol. 20, pages 289-352, report a study carried out on various metal oxides for determining their dehydrating and dehydrogenating properties in the dehydration reaction of ethyl alcohol to ethylene.

Efforts have been made in the art to avoid the deactivation of dehydration catalysts and/or to enhance the yield of the dehydration processes using them.

U.S. Pat. No. 2,426,678, for example, describes a method for regenerating dehydration catalysts based on phosphates, preferably ammonium phosphate, using volatile esters of phosphoric acid, whose industrial application is, in any case, complex and expensive.

U.S. Pat. No. 2,399,164 describes a process for the preparation of 1,3-butadiene, or of other unsaturated hydrocarbons, starting from 1,3-butanediol or from other polyhydroxy compounds, by diluting said 1,3-butanediol or said polyhydroxy compounds, in vapour form, with a suitable quantity of 1,3-butadiene or of said unsaturated hydrocarbons in the form of gas or vapour, in the presence of a dehydration catalyst (for example, a mixture of calcium monophosphate, sodium monophosphate ethylamine phosphate and phosphoric acid). The above process is said to be capable of increasing the yield of 1,3-butadiene or of unsaturated hydrocarbons and of reducing, or even eliminating, the formation of oily polymers. Also in this case, however, the dilution of said 1,3-butanediol or of said polyhydroxy compounds makes the industrial application of this process inconvenient.

U.S. Pat. No. 2,373,153 describes a process for enhancing the dehydration of 1,3-butanediol to produce 1,3-butadiene comprising feeding 1,3-butanediol and a certain quantity of volatile basic material (for example, ammonia; volatile substituted amines such as, for example, primary, secondary or tertiary ethyl-, propyl-, butyl-amines, aniline, pyridine, or materials which decompose under the reaction conditions to give volatile bases such as, for example, urea), to a chamber containing an acidic dehydration catalyst (preferably, ammonium phosphate). The use of said volatile basic material is said to guarantee a prolonged activity of the catalyst and to improve the efficiency of the process.

Numerous efforts have been made in the art to find catalysts suitable for the dehydration of alcohols to give olefins and dienes.

English patent GB 1,275,171, for example, describes a process for the preparation of a catalyst based on lithium phosphate to be used in the dehydration of an epoxide or of a diol to give a diene. The use of said catalyst in the dehydration of epoxides or of diols to give dienes is said to allow the production, as by-products, of mainly carbonyl compounds which can be reconverted to olefins. Furthermore, said catalyst is said to have the advantage to be calcined at 600° C. without losing its activity, to enable it to be regenerated after use.

U.S. Pat. No. 2,420,477 describes a process for the preparation of butadiene comprising reacting vinyl ethyl ether with ethylene within a temperature range of 125° C.-250° C., in the presence of a catalyst comprising a "core" of a metal selected from the group consisting of beryllium, magnesium, zinc, cadmium, aluminium, or alloys thereof, said "core" being covered with a metal oxide such as, for example, vanadium, niobium, tantalum, chromium, molybdenum, tungsten and uranium.

The above-mentioned process is said to be carried out at temperatures lower than those normally used for the preparation of butadiene and substantially to be capable of avoiding the production of by-products.

International patent application WO 2013/017496 describes the use of a catalyst comprising a phosphorous-modified zeolite for the dehydration of alcohols to give low-molecular-weight olefins, said catalyst being obtained through a specific process which is said to be easily reproducible and that gives a catalyst having good performances.

American patent U.S. Pat. No. 4,260,845 describes the dehydration of a saturated alcohol to olefin in the presence of a dehydration catalyst based on zinc aluminate having a molar ratio $ZnO/Al_2O_3$ of about 1, said catalyst having been heated in the air for a time and to a temperature sufficient for its activation. The above catalyst is said to have good performances in terms of selectivity.

In spite of the efforts made in the art, the objective of finding dehydration catalysts having good performances and a longer duration, and/or processes which can increase the life of said catalysts and/or reduce the formation of by-products which, as mentioned above, can cause poisoning of the catalyst, still remains and is consequently of great interest.

The Applicant has therefore considered the problem of finding a process for the dehydration of oxygenated compounds, in particular saturated alcohols, unsaturated alcohols, diols, ethers, which can increase the duration of the dehydration catalyst used and/or reduce the formation of by-products.

The Applicant has now found that the use of at least one basic agent, selected from ammonia ($NH_3$), or from inorganic or organic compounds containing nitrogen capable of developing ammonia ($NH_3$) during the dehydration process of oxygenated compounds, in particular saturated alcohols, unsaturated alcohols, diols, ethers, and optionally of silica ($SiO_2$), or of at least a catalyst for the dissociation of ammonia ($NH_3$) selected from catalysts comprising silica ($SiO_2$), allows the life of the dehydration catalyst used to be increased, and/or to reduce the formation of by-products. In particular, the Applicant has found that the use of said basic agent, and optionally of silica ($SiO_2$), or of at least a catalyst for the dissociation of ammonia ($NH_3$) selected from catalysts comprising silica ($SiO_2$), is capable, in the presence of a dehydration catalyst selected from cerium oxide ($CeO_2$), aluminium oxide ($\gamma$-$Al_2O_3$), aluminium silicate, silica-aluminas ($SiO_2$—$Al_2O_3$), aluminas, zeolites, sulfonate resins, ion-exchange resins, metal oxides (for example, lanthanum oxide, zirconium oxide, tungsten oxide, thallium oxide, magnesium oxide, zinc oxide), ammonium phosphate, metal phosphates such as, for example, boron phosphate, aluminium phosphate, calcium phosphate, sodium phosphate, cerium phosphate, of increasing the life of the catalyst and consequently the productivity of the same, and/or reduce the formation of by-products, in particular the formation of carbonyl compounds, more specifically of acetaldehyde and of methyl-vinyl ketone.

An object of the present invention therefore relates to a process for the dehydration of at least one oxygenated compound, preferably selected from saturated alcohols, unsaturated alcohols, diols, ethers, in the presence of at least one dehydration catalyst selected from cerium oxide ($CeO_2$), aluminium oxide ($\gamma$-$Al_2O_3$), aluminium silicate, silica-aluminas ($SiO_2$—$Al_2O_3$), aluminas, zeolites, sulfonate resins, ion-exchange resins, metal oxides (for example, lanthanum oxide, zirconium oxide, tungsten oxide, thallium oxide, magnesium oxide, zinc oxide); of at least one basic agent selected from ammonia ($NH_3$), or from inorganic or organic compounds containing nitrogen capable of developing ammonia ($NH_3$) during said dehydration process; and, optionally, of silica ($SiO_2$), or of at least one catalyst for the dissociation of ammonia ($NH_3$) selected from catalysts comprising silica ($SiO_2$), preferably of silica ($SiO_2$).

For the purposes of the present description and of the following claims, the definitions of the numerical ranges always include the extremes unless otherwise specified.

For the purposes of the present description and of the following claims, the term "comprising" also includes the terms "which essentially consists of" or "which consists of".

According to a further aspect, the present invention also relates to a dehydration process for the dehydration of at least one oxygenated compound, preferably selected from saturated alcohols, unsaturated alcohols, diols, ethers, comprising feeding to a reactor including at least a first catalytic bed comprising silica ($SiO_2$), or at least a first catalytic bed comprising at least one catalyst for the dissociation of ammonia ($NH_3$) selected from catalysts comprising silica ($SiO_2$), preferably at least a first catalytic bed comprising silica ($SiO_2$), and at least a second catalytic bed comprising at least one dehydration catalyst selected from cerium oxide ($CeO_2$), aluminium oxide ($\gamma$-$Al_2O_3$), aluminium silicate, silica-aluminas ($SiO_2$—$Al_2O_3$), aluminas, zeolites, sulfonate resins, ion-exchange resins, metal oxides (for example, lanthanum oxide, zirconium oxide, tungsten oxide, thallium oxide, magnesium oxide, zinc oxide), a mixture comprising said at least one oxygenated compound and at least one basic agent selected from ammonia ($NH_3$), or from inorganic or organic compounds containing nitrogen capable of developing ammonia ($NH_3$) during said dehydration process, said mixture being fed to said reactor so as to pass first through said first catalytic bed and subsequently through said second catalytic bed.

According to a further aspect, the present invention also relates to a process for the dehydration of at least one oxygenated compound, preferably selected from saturated alcohols, unsaturated alcohols, diols, ethers, comprising feeding to a reactor including at least a first catalytic bed comprising silica ($SiO_2$), or at least a first catalytic bed comprising at least one catalyst for the dissociation of ammonia ($NH_3$), selected from catalysts comprising silica ($SiO_2$), preferably at least a first catalytic bed comprising silica ($SiO_2$), and at least a second catalytic bed comprising at least one dehydration catalyst selected from ammonium phosphate or from phosphates of metals such as, for example, boron phosphate, aluminium phosphate, calcium phosphate, sodium phosphate, cerium phosphate, preferably calcium phosphate, a mixture comprising said at least one oxygenated compound and at least one basic agent selected from ammonia ($NH_3$), or from inorganic or organic compounds containing nitrogen capable of developing ammonia ($NH_3$) during said dehydration process, said mixture being fed to said reactor so as to pass first through said first catalytic bed and subsequently through said second catalytic bed.

For the purposes of the present description and of the following claims, the term phosphate should be intended in its widest meaning, i.e. comprising, where existing, the mono- or di-acidic form of the phosphate (for example, sodium mono-acid phosphate, sodium di-acid phosphate, calcium mono-acid phosphate), and mixtures thereof.

According to a preferred embodiment of the present invention, said saturated alcohols can be selected, for example, from alcohols having from 1 to 25 carbon atoms, preferably from 2 to 20 carbon atoms. Said saturated alcohols can preferably be selected, for example, from: methanol, ethanol, 1-propanol, 2-propanol, 1-butanol, 2-butanol, 3-methyl-1-butanol, 1-pentanol, 1-hexanol, or mixtures thereof. Ethanol, 2-propanol, 1-butanol, 3-methyl-1-butanol, 1-hexanol, or mixtures thereof, are preferred.

According to a preferred embodiment of the present invention, said unsaturated alcohols can be selected, for example, from unsaturated alcohols having from 2 to 20 carbon atoms, preferably from 4 to 15 carbon atoms. Said unsaturated alcohols can preferably be selected, for example, from: allyl alcohol, 2-buten-1-ol (crotyl alcohol), 3-buten-1-ol (allylcarbinol), 3-buten-2-ol (methylvinylcarbinol), 2-methyl-3-buten-2-ol, 2-methyl-3-buten-1-ol, 2-methyl-2-buten-1-ol, 3-methyl-2-buten-1-ol, 3-methyl-3-buten-1-ol, 2-methyl-3-buten-2-ol, or mixtures thereof; 2-buten-1-ol (crotyl alcohol), 3-buten-1-ol (allylcarbinol), 3-buten-2-ol (methylvinylcarbinol), 3-methyl-2-buten-1-ol, 3-methyl-3-buten-1-ol, 2-methyl-3-buten-2-ol, or mixtures thereof, are preferred.

According to a preferred embodiment of the present invention, said diols can be selected, for example, from diols having from 2 to 20 carbon atoms, preferably from 4 to 15 carbon atoms. Said diols can preferably be selected, for example, from: ethylene glycol, propanediol, 1,3-butanediol, 1,4-butanediol, pentanediol, 2-methyl-propanediol, 2,2-dimethyl-propanediol, hexanediol, decanediol, or mixtures thereof. 1,3-butanediol, 1,4-butanediol, or mixtures thereof, are preferred.

According to a preferred embodiment of the present invention, said ethers can be selected, for example, from cyclic or linear ethers having from 4 to 12 carbon atoms, such as, for example, methyl-tert-butylether, diethyl ether, tert-amyl methyl ether, tetrahydrofuran. Tetrahydrofuran is preferred.

According to a preferred embodiment of the present invention, said saturated alcohols, unsaturated alcohols, diols, ethers, can be used in anhydrous form, or mixed with water, said water being present in a quantity higher than or equal to 0.005% by weight, preferably ranging from 10% by weight to 85% by weight, more preferably ranging from 15% by weight to 30% by weight, with respect to the total weight of said mixture.

According to a preferred embodiment of the present invention, said oxygenated compounds, preferably said saturated alcohols, unsaturated alcohols, diols, ethers, derive from the fermentation of sugars obtained from biomass.

According to a further aspect, the present invention relates to a process comprising:
- subjecting 1,3-butanediol to dehydration, preferably in a mixture with water, said 1,3-butanediol being preferably obtained from the fermentation of sugars obtained from biomass, in the presence of at least one dehydration catalyst selected from cerium oxide ($CeO_2$), aluminium oxide ($\gamma$-$Al_2O_3$), aluminium silicate, silica-aluminas ($SiO_2$—$Al_2O_3$), aluminas, zeolites, sulfonate resins, ion-exchange resins, metal oxides (for example, lanthanum oxide, zirconium oxide, tungsten oxide, thallium oxide, magnesium oxide, zinc oxide), preferably cerium oxide ($CeO_2$); of at least one basic agent selected from inorganic or organic compounds containing nitrogen capable of developing ammonia ($NH_3$) during said dehydration; and optionally, of silica ($SiO_2$), or of at least one catalyst for the dissociation of ammonia ($NH_3$) selected from catalysts comprising silica ($SiO_2$), preferably of silica ($SiO_2$), obtaining unsaturated alcohols;
- subjecting the unsaturated alcohols obtained as described above to distillation and to a further dehydration, in the presence of at least one dehydration catalyst selected from aluminium oxide ($\gamma$-$Al_2O_3$), aluminium silicate, silica-aluminas ($SiO_2$—$Al_2O_3$), aluminas, zeolites, sulfonate resins, ion-exchange resins, acid earth (for example, lanthanum oxide, zirconium oxide), preferably silica-aluminas ($SiO_2$—$Al_2O_3$); of at least one basic agent selected from inorganic or organic compounds containing nitrogen capable of developing ammonia ($NH_3$) during said dehydration; and, optionally, of silica ($SiO_2$), or of at least one catalyst for the dissociation of ammonia ($NH_3$) selected from catalysts comprising silica ($SiO_2$), preferably of silica ($SiO_2$), obtaining 1,3-butadiene.

Said 1,3-butadiene can be advantageously used as monomer or as intermediate in the production of elastomeric materials, thermoplastic materials, and also materials based on (co)polymers.

For the purposes of the present description and of the following claims, the term "biomass" indicates any organic material of a vegetable origin including: products deriving from agriculture such as, for example, guayule, thistle, corn, soybean, cotton, linseed, rapeseeds, sugar cane, palm oil, comprising scraps, residues and waste products deriving from said products or from their processing; products deriving from crops specifically cultivated for energy use, such as, for example, miscanthus, foxtail millet, common cane, comprising scraps, residues and waste products deriving from said products or from their processing; products deriving from forestation or silviculture comprising scraps, residues and waste products deriving from said products or from their processing; scraps of agro-food products destined for human nutrition or zootechnics; residues from the paper industry; waste products coming from the differentiated collection of solid urban waste, such as, for example, urban waste of a vegetable origin, paper.

According to a particularly preferred embodiment of the present invention, said saturated alcohols, unsaturated alcohols, diols, ethers, derive from the fermentation of sugars obtained from guayule or from thistle, comprising scraps and residues deriving from said guayule and/or thistle or from their processing.

According to an even more preferred embodiment of the present invention, said saturated alcohols, unsaturated alcohols, diols, ethers, derive from the fermentation of sugars obtained from guayule, comprising scraps and residues deriving from said guayule or from its processing.

The production of sugars from biomass can be carried out using processes known in the art.

For example, in the case of the use of a biomass of a vegetable origin (for example, a lignocellulosic biomass) for producing sugars, said biomass is subjected to physical treatments (for example, extrusion, steam explosion, and the like) and/or to chemical hydrolysis and/or to enzymatic hydrolysis, obtaining mixtures of carbohydrates, aromatic compounds and other products deriving from cellulose, hemicellulose and lignin present in the biomass. In particular, the carbohydrates obtained are mixtures of sugars with 5 or 6 carbon atoms including, for example, sucrose, glucose, xylose, arabinose, galactose, mannose and fructose, to be used in the fermentation. Further details relating to processes for the production of sugars from biomass can be found, for example, in Italian patent application MI2013A002069, in the name of the Applicant. Said fermentation is generally carried out by microorganisms, in particular genetically modified microorganisms, capable of producing alcohols of interest. More details on processes for the synthesis of 1,3-butanediol starting from biomass can be found, for example, in US patent applications US 2010/330635, US 2012/329113, US 2013/066035, US 2013/109064.

For the purposes of the present invention, said dehydration catalysts can contain binders such as, for example, alumina, silica, and/or optionally being supported on inert carriers such as, for example, pumice, graphite, silica.

For the purposes of the present description and of the following claims, the term "zeolites" is intended in its wider meaning, i.e. also comprising materials commonly known as, for example, "zeolite-like", "zeotype"; zeolites modified with phosphorous, or with a metal such as, for example, sodium, potassium, boron, or with a metal of the lanthanide series; and the like.

According to a preferred embodiment of the present invention, said basic agent can be selected, for example, from ammonia ($NH_3$) in gaseous form; ammonium hydroxide ($NH_4OH$); urea; ammonium carbonate or bicarbonate; aliphatic or aromatic primary, secondary or tertiary amines, having a boiling point ranging from −8° C. to 250° C. such as, for example, n-butylamine, methyl amine, ethyl amine, diethyl amine, propyl amine, aniline, or mixtures thereof; heterocyclic compounds containing one or more nitrogen atoms such as, for example, pyrrole. Said basic agent can optionally be used in aqueous solution. Ammonia ($NH_3$) in gaseous form, ammonium hydroxide ($NH_4OH$), urea, ammonium carbonate or bicarbonate, n-butyl amine, pyrrole, or mixtures thereof, are preferred.

According to a preferred embodiment of the present invention, said basic agent can be used in such a quantity so as to have a concentration of ammonia ($NH_3$), or an equivalent concentration of ammonia ($NH_3$), referring to the total weight of said at least one oxygenated compound and of other organic compounds optionally present, ranging from 0.005% by weight to 4% by weight, preferably ranging from 0.1% by weight to 3% by weight, more preferably ranging from 0.5% by weight to 2% by weight.

For the purposes of the present description and of the following claims, the term "other organic compounds present" refers to organic compounds such as, for example, $C_2$-$C_4$ alcohols, carbonyl compounds (such as, for example, acetone, butanone, butanal), and the like, which can be present in the mixture subjected to dehydration.

In accordance with a preferred embodiment of the present invention, said silica ($SiO_2$) can be present as binder or as carrier of the dehydration catalyst, preferably as binder.

In accordance with a further preferred embodiment of the present invention, said silica ($SiO_2$), when added, can be added in a quantity ranging from 1% by volume to 100% by volume, preferably ranging from 5% by volume to 90% by volume, with respect to the total volume of the dehydration catalyst.

It should be noted that, for the purposes of the present invention, as it is evident from the processes indicated above object of the present invention, when said silica or said catalyst for the dissociation of ammonia ($NH_3$) comprising silica ($SiO_2$), are added, they are added as catalytic bed in the reactor where the above process is carried out.

In accordance with a preferred embodiment of the present invention, said catalyst for the dissociation of ammonia ($NH_3$) comprising silica ($SiO_2$), can be selected, for example, from catalysts comprising, in addition to silica ($SiO_2$), iron oxides (for example, magnetite), aluminium oxide, calcium oxide, potassium oxide.

Further details relating to said catalyst for the dissociation of ammonia ($NH_3$) comprising silica ($SiO_2$) can be found, for example, in American patent U.S. Pat. No. 3,979,336.

In accordance with a further preferred embodiment of the present invention, said catalyst for the dissociation of ammonia ($NH_3$) comprising silica ($SiO_2$), when added, can be added in a quantity ranging from 1% by volume to 100% by volume, preferably ranging from 5% by volume to 90% by volume, with respect to the total volume of the dehydration catalyst.

In accordance with a preferred embodiment of the present invention, said dehydration process of oxygenated compounds can be carried out, in continuous, in a reactor. Said reactor can be a fixed-bed or a fluid-bed reactor, preferably a fixed-bed. Said reactor can be adiabatic, isotherm, or a combination of the two, preferably adiabatic.

In accordance with a preferred embodiment of the present invention, said reactor can operate at a temperature ranging from 190° C. to 500° C., preferably ranging from 240° C. to 450° C., more preferably ranging from 280° C. to 430° C.

In accordance with a preferred embodiment of the present invention, said reactor can operate at a pressure ranging from 0.3 bara (absolute bar) to 3.5 bara (absolute bar), preferably ranging from 0.6 bara (absolute bar) to 2.5 bara (absolute bar), more preferably ranging from 0.8 bara (absolute bar) bar to 1.8 bara (absolute bar).

In accordance with a preferred embodiment of the present invention, said at least one oxygenated compound can be fed to said reactor operating at a "Weight Hourly Space Velocity" (WHSV), i.e. at a ratio between the total weight of said at least one oxygenated compound, and optionally water, fed in an hour, and the weight of the dehydration catalyst, said ratio being measured as $h^{-1}$, ranging from 0.5 $h^{-1}$ to 30 $h^{-1}$, preferably ranging from 1 $h^{-1}$ to 20 $h^{-1}$, more preferably ranging from 2 $h^{-1}$ to 15 $h^{-1}$.

It should be noted that in order to avoid fluidization phenomena of the catalyst, a feeding to said reactor with a down-flow configuration is preferred.

Some illustrative and non-limiting examples are provided hereunder for a better understanding of the present invention and for its practical embodiment.

EXAMPLE 1

Preparation of 1,3-butadiene (1,3-BDE) by means of two dehydration reactions carried out in series starting from a mixture of 1,3-butanediol (1,3-BDO)

Part I—First Dehydration Reaction of 1,3-BDO to Unsaturated Alcohols

A mixture of 1,3-BDO, ammonium hydroxide ($NH_4OH$) and water, having a weight concentration respectively equal to 82.0% of 1,3-BDO, 1.2% of ammonium hydroxide ($NH_4OH$) and 16.8% of water (mixture 1), was prepared for this purpose and then used for the first dehydration reaction. The equivalent concentration of ammonia ($NH_3$) in said mixture 1 is equal to 0.5% by weight with respect to the total weight of 1,3-BDO.

The reactor in which said first dehydration reaction was carried out was composed of an AISI 304 stainless steel tubular element having a height (h) equal to 260 mm and an internal diameter ($\Phi$) equal to 10 mm, preceded by and connected to an evaporator, both equipped with electrical heating. The outlet of the reactor, on the other hand, was connected to a first condenser connected to a collection flask, and operating at 15° C., in order to allow the recovery of the products obtained from the first dehydration reaction in liquid form at room temperature (25° C.) in said collection flask. Said collection flask was, in turn, connected to a sampling system consisting of a steel cylinder having a volume (V) equal to 300 ml and equipped, at the two ends, with interception valves. The vapours/gases deriving from the first dehydration reaction and optionally not condensed in the system previously described, could also flow through the above-mentioned steel cylinder, in turn connected to a flow meter which measured their quantity.

The products obtained, both in liquid form and in the form of vapour/gas, were characterized through gas-chromatography, using:

for products in liquid form, a Thermo Trace gas-chromatograph equipped with a FID detector and AQUA-WAX column (Grace 30 m length×0.53 mm internal diameter×1.0 µm film thickness);

for products in the form of vapour/gas, a 490 micro GC Varian/Agilent gas-chromatograph equipped with 4 channels and with the following columns: Pora Plot Q 10 m long, MolSieve 5 Å 4 m long, $Al_2O_3$ 10 m long with "backflush" functionality, CPSil-19 CB 7.5 m long.

The catalyst used in said first dehydration reaction was a material based on Cerium Oxide ($CeO_2$) in granules having dimensions ranging from 0.5 mm to 1 mm and was charged into said reactor in a quantity equal to 10 g (3.5 ml). Said catalyst was specifically prepared following the laboratory procedure described hereunder.

For this purpose, 500 g of a commercial aqueous solution of about 30% of ammonium hydroxide ($NH_4OH$), (28%-30% $NH_3$ Basis ACS reagent Aldrich) were added with 500 g of water in a first 3-litre beaker, equipped with a stirring rod having a half-moon Teflon blade, and an electrode was introduced for the measurement of the pH [Metrohm glass electrode for pH (6.0248.030), connected to the pH-meter Metrohom 780]. A solution of 100 g of cerium nitrate hexahydrate (99% Aldrich) was prepared in 1,000 g of water in a second 2-litre beaker, equipped with a magnetic stirrer: the cerium nitrate hexahydrate was then solubilized by vigorous stirring at room (25° C.) temperature.

The solution obtained was introduced into a dripper and fed dropwise, over a period of 2 hours, to the ammonium hydroxide solution contained in the 3-litre beaker indicated above, under constant vigorous stirring. The pH of the suspension obtained was equal to 10.2. The solid in suspension was filtered, washed with 2 litres of water and then dried in an oven at 120° C., for 2 hours. The synthesis was repeated until 2,000 g of solid had been obtained.

1,270 g of the solid thus obtained were introduced, after sieving at 0.125 mm, into an extruder to which 175.9 g of a solution at 25% of ammonium hydroxide ($NH_4OH$) (obtained by diluting the $NH_3$ solution at 28%-30% Basis ACS reagent Aldrich) were also fed by means of a Watson Marlow peristaltic pump set to 5 rpm. At the end of this feeding, 158 g of demineralized water were also fed: in this way the correct consistency for the extrusion was obtained. The pellets obtained at the outlet of the extruder were dried in the air and a portion equal to 100 g was subsequently calcined at 800° C. with a temperature ramp of 1° C./minute up to 800° C. followed by an isotherm at that temperature for 6 hours. The calcined solid was granulated and sieved and the fraction of granules having dimensions ranging from 0.5 mm to 1 mm was used as catalyst.

Said first dehydration reaction was then carried out by feeding the mixture 1, first to the above-mentioned evaporator previously heated to a temperature equal to 250° C., and from this to the above-mentioned tubular reactor previously heated so as to have an internal temperature, during the dehydration reaction, equal to 400° C. Both the evaporator and the reactor were maintained at atmosphere pressure (1 bara).

The flow-rate of mixture 1 fed to the evaporator was equal to 100 g/h, whereas the flow-rate fed to the reactor, expressed as WHSV, was equal to 10 $h^{-1}$.

The test was carried out for a time sufficient for collecting an adequate amount of products, collected in both liquid form and in the form of vapour/gas which, when subjected to gas-chromatographic analysis, showed the composition indicated in Table 1 for the liquid fraction (mixture 2), with particular reference to the presence of undesired by-products containing a carbonyl group. These carbonyl compounds, expressed in relation to the unsaturated alcohols which, on the other hand, represent the desired products in the first dehydration reaction, are grouped into two categories:
methylvinylketone+acetaldehyde
other carbonyl compounds (acetone, butanone, butanal, etc.)
and were calculated according to the following formula:

$$r_{C/A} = \frac{\sum_i carb_i}{\sum_i alc_i} \times 100;$$

wherein:
$r_{C/A}$=grams of carbonyl compounds per 100 g of unsaturated alcohols produced;
$carb_i$=grams of i-th carbonyl compound produced [referring to methylvinylketone, acetaldehyde, other carbonyl compounds];
$alc_i$=grams of i-th unsaturated alcohol produced
[referring to 3-buten-2-ol (methylvinylcarbinol) and to 2-buten-1-ol (crotyl alcohol)]

TABLE 1

| $NH_3$ equivalents (%) | Acetaldehyde + methylvinylketone (g/100 g of unsaturated alcohols) | Other carbonyl compounds (g/100 g of unsaturated alcohols) |
|---|---|---|
| 0.5 | 0.57 | 0.80 |

Part II Second Dehydration Reaction of Unsaturated Alcohols to 1,3-BDE

Mixture 2 previously obtained as described above, was subjected to purification, by means of distillation, in order to remove the non-reacted 1,3-butanediol. Said distillation was carried out at atmospheric pressure, adding 3,5-di-tert-4-butylhydroxytoluene (BHT) to mixture 2 present in the boiler of the distillation column, so as to have a concentration of the same in said mixture 2 equal to about 200 ppm. Said distillation was carried out using an Oldershaw column having 40 plates (2 segments of 20 plates), charging said mixture 2 into the boiler in a single tranche and condensing and collecting the cut at the head, included within the temperature range of 103.1° C. to 210.0° C., and progressively concentrating the heaviest components in the boiler. Said head cut (mixture 3) was characterized by the following final composition by weight:
unsaturated alcohols (3-buten-2-ol and 2-buten-1-01) equal to 60%;
water equal to 38%;
other compounds ($C_2$-$C_4$ alcohols, carbonyl compounds, etc.) equal to 2%.

Two catalytic beds were parallelly charged in series, in a reactor analogous to the previous reactor. A first catalytic bed was therefore charged in a quantity equal to 4 g (5.2 ml) of silica ($SiO_2$) obtained starting from colloidal silica (Ludox® TMA—Sigma-Aldrich) according to the laboratory procedure described hereunder.

For this purpose, 400.0 g of colloidal silica (Ludox® TMA—Sigma-Aldrich) were charged into a 800 ml beaker and the whole mixture was kept under vigorous stirring (500 rpm), on a heating plate at 150° C., until it was dry. The solid obtained was dried in an oven at 120° C., for 12 hours, and subsequently calcined at 600° C., for 5 hours, obtaining 136.5 g of a colourless product. The product obtained was granulated mechanically and the fraction of granules having dimensions ranging from 0.5 mm to 1.0 mm was used as in said first catalytic bed.

A second catalytic bed was subsequently charged, in a quantity equal to 4 g (10 ml), with a catalyst based on a material specifically prepared according to the laboratory procedure described hereunder.

For this purpose, 7.55 g of aluminium tri-sec-butoxide (Aldrich) were introduced into a first 500 ml flask, as alumina precursor ($Al_2O_3$), and 50.02 g of orthosilicic acid (Aldrich, <20 mesh), were introduced, as silica precursor ($SiO_2$), into a second 500 ml flask with 250.02 g of demineralized water. The suspension of orthosilicic acid obtained was slowly added (10 minutes) to said first flask containing aluminium tri-sec-butoxide, and the mixture obtained was maintained at 90° C., for about 1 hour, under vigorous stirring (500 rpm). After cooling to room temperature (25° C.), the suspension obtained was filtered and the solid obtained was washed with 5 litres of demineralized water, dried at 120° C. for a night and subsequently calcined at 500° C. for 5 hours obtaining a colourless powder (47.95 g) (called "active phase").

Part of the above-mentioned active phase (40.42 g) was mixed with 24.43 g of pseudoboehmite Versal™ V-250 (UOP), as alumina precursor ($Al_2O_3$) of the binder, and 302 ml of a solution at 4% of acetic acid, in a 800 ml beaker. The mixture obtained was kept under stirring at 60° C., for about 2 hours. The beaker was subsequently transferred to a heating plate and the mixture was heated, under vigorous stirring, for a night, at 150° C., until it was dry. The solid obtained was subsequently calcined at 550° C., for 5 hours, obtaining 60.45 g of a colourless product which was granulated mechanically, the fraction of granules having dimensions ranging from 0.1 mm to 1.0 mm was used as dehydration catalyst in said second catalytic bed.

Parallelly, a quantity of ammonium hydroxide (NH$_4$OH) was added to mixture 3 prevalently containing unsaturated alcohols, operating according to the same procedure described above, so as to have an equivalent concentration of ammonia (NH$_3$) equal to 1.0% by weight with respect to the total weight of the compounds present in said mixture 3 [i.e. unsaturated alcohols (3-buten-2-ol and 2-buten-1-ol) and other compounds (C$_2$-C$_4$ alcohols, carbonyl compounds, etc.)]. The new mixture thus obtained was fed, in the form of vapour and at a flow-rate expressed as WHSV (referring to the dehydration catalyst) equal to 3.3 h$^{-1}$, to the reactor, previously charged with said first catalytic bed and with said second catalytic bed as indicated above, operating at atmospheric pressure (1 bara) and at a temperature equal to 300° C., so that said mixture passed first through said first catalytic bed and subsequently through said second catalytic bed.

The second dehydration reaction was then carried out for a time sufficient for collecting an adequate quantity of products collected in both liquid form and in the form of vapour/gas which, when subjected to gas-chromatographic analysis allowed the parameters indicated in Table 2, to be calculated in terms of conversion of the unsaturated alcohols (C$_{ALCH.}$) and selectivity to 1,3-BDE (S$_{1,3-BDE}$) determined according to the formulae indicated hereunder.

$$C_{ALCH.} = \frac{(moles_{ALCH.})_{in} - (moles_{ALCH.})_{out}}{(moles_{ALCH.})_{in}} \times 100;$$

$$S_{1,3-BDE} = \frac{moles_{1,3-BDE}}{(moles_{ALCH.})_{in} - (moles_{ALCH.})_{out}} \times 100;$$

wherein:
(moles$_{ALCH.}$)$_{in}$=moles of unsaturated alcohols at the inlet;
(moles$_{ALCH.}$)$_{out}$=moles of unsaturated alcohols at the outlet;
moles$_{1,3-BDE}$=total moles of 1,3-butadiene.

TABLE 2

| NH$_3$ equivalents (%) | Duration of dehydration (hours) | Conversion (%) | Selectivity (%) |
|---|---|---|---|
| 1.0 | 8 | 100[2] | 86[1] |
|  | 128 | 83[2] | 92[1] |

[1]values referring to 1,3-BDE;
[2]values referring to unsaturated alcohols.

The test was interrupted after 128 hours of continuous running, when the conversion and selectivity values reported in Table 2 had become stabilized.

EXAMPLE 2 (comparative)

Preparation of 1,3-butadiene (1,3-BDE) by means of two dehydration reactions carried out in series starting from a mixture of 1,3-butanediol (1,3-BDO)

Example 2 was carried out under the same operating conditions described above for Example 1, with the exception that:
in Part I ammonium hydroxide (NH$_4$OH) was not used;
in Part II ammonium hydroxide (NH$_4$OH) was not used;
in Part II the first catalytic bed comprising silica (SiO$_2$) was not used.

The results obtained are indicated in Table 3 for Part I and in Table 4 for Part II.

TABLE 3

| NH$_3$ equivalents (%) | Acetaldehyde + methylvinylketone (g/100 g of unsaturated alcohols) | Other carbonyl compounds (g/100 g of unsaturated alcohols) |
|---|---|---|
| 0.0 | 3.01 | 1.81 |

The values indicated in Table 3 show a formation of carbonyl compounds as by-products in the first dehydration reaction (Part I) which is much higher than those obtained in Example 1 and indicated in Table 1.

TABLE 4

| NH$_3$ equivalents (%) | Duration of dehydration (hours) | Conversion (%) | Selectivity (%) |
|---|---|---|---|
| 0.0 | 8 | 100[2] | 85[1] |
|  | 54 | 74[2] | 76[1] |

[1]values referring to 1,3-BDE;
[2]values referring to unsaturated alcohols.

The test was interrupted after only 54 hours of continuous running, when the conversion and selectivity values indicated in Table 4 had dropped well below those obtained in Example 1 and indicated in Table 2, due to a high deactivation of the catalyst used in the second dehydration reaction (Part II).

EXAMPLE 3 (comparative)

Preparation of 1,3-butadiene (1,3-BDE) by means of two dehydration reactions carried out in series starting from a mixture of 1,3-butanediol (1,3-BDO)

Example 3 was carried out under the same operating conditions described above for Example 1, with the exception that:
in Part II, a quantity of ammonium hydroxide (NH$_4$OH) was added so as to have an equivalent concentration of ammonia (NH$_3$) equal to 0.1% with respect to the total weight of the compounds present in said mixture 3 [i.e. unsaturated alcohols (3-buten-2-ol and 2-buten-1-ol) and other compounds (C$_2$-C$_4$ alcohols, carbonyl compounds, etc.)], instead of being equal to 1.0% by weight as indicated in Example 1;
in Part II, the first catalytic bed comprising silica (SiO$_2$) was not used.

The results obtained, only for the Part II, are indicated in Table 5.

TABLE 5

| NH$_3$ equivalents (%) | Duration of dehydration (hours) | Conversion (%) | Selectivity (%) |
|---|---|---|---|
| 0.1 | 8 | 99[2] | 87[1] |
|  | 24 | 69[2] | 69[1] |

[1]values referring to 1,3-BDE;
[2]values referring to unsaturated alcohols.

The test was interrupted after only 24 hours of continuous running, when the conversion and selectivity values indicated in Table 5 had dropped well below those obtained in Example 1 and indicated in Table 2, due to a high deactivation of the catalyst used in the second dehydration reaction (Part II).

EXAMPLE 4

Preparation of 1,3-butadiene (1,3-BDE) by means of two dehydration reactions carried out in series starting from a mixture of 1,3-butanediol (1,3-BDO)

Example 4 was carried out under the same operating conditions described above for Example 1, with the exception that:

in Part II, a quantity of ammonium hydroxide (NH$_4$OH) was added so as to have an equivalent concentration of ammonia (NH$_3$) equal to 1.2% with respect to the total weight of the compounds present in said mixture 3 [i.e. unsaturated alcohols (3-buten-2-ol and 2-buten-1-ol) and other compounds (C$_2$-C$_4$ alcohols, carbonyl compounds, etc.)], instead of being equal to 1.0% by weight as indicated in Example 1;

in Part II, a different dehydration catalyst was used having silica (SiO$_2$) as binder prepared as described hereunder, for the second catalytic bed;

in Part II, the second dehydration reaction was carried out maintaining the reactor at a temperature of 350° C.;

in Part II, the first catalytic bed comprising silica (SiO$_2$) was not used.

For preparing the dehydration catalyst, 7.6 g of aluminium tri-sec-butoxide (Aldrich), were introduced into a first 500 ml flask, as alumina precursor (Al$_2$O$_3$), and 50 g of orthosilicic acid (Aldrich, <20 mesh), were introduced into a second 500 ml flask, as silica precursor (SiO$_2$), with 250.09 g of demineralized water. The suspension of orthosilicic acid obtained was added slowly (10 minutes) to said first flask containing aluminium tri-sec-butoxide, and the mixture obtained was maintained at 90° C., for about 1 hour, under vigorous stirring (500 rpm). After cooling to room temperature (25° C.), the suspension obtained was filtered, the solid obtained was washed with 5 litres of demineralized water, dried in an oven at 120° C., for a night, and subsequently calcined at 500° C., for 5 hours, obtaining a colourless powder (52.23 g) (called "active phase").

Part of the above-mentioned active phase (41.10 g) was mixed with 52.72 g of colloidal silica (SiO$_2$) (Ludox® TMA—Sigma-Aldrich), as silica precursor (SiO$_2$) of the binder, and 150 ml of demineralized water in a 500 ml beaker: the mixture obtained was kept under stirring at 60° C., for about 2 hours. The beaker was subsequently transferred to a heating plate and the mixture was heated, under vigorous stirring, for a night, at 150° C., until it was dry. The solid obtained was calcined at 550° C., for 5 hours, obtaining a colourless solid which was granulated mechanically. 4 g (9.3 ml) of the fraction of granules having dimensions ranging from 0.1 mm to 1.0 mm was used as catalyst.

The results obtained, only for the Part II, are indicated in Table 6.

TABLE 6

| NH$_3$ equivalents (%) | Duration of dehydration (hours) | Conversion (%) | Selectivity (%) |
|---|---|---|---|
| 1.2 | 8 | 100$^{(2)}$ | 90$^{(2)}$ |
|  | 76 | 42$^{(1)}$ | 81$^{(1)}$ |

$^{(1)}$values referring to 1,3-BDE;
$^{(2)}$values referring to unsaturated alcohols.

The test was interrupted after 76 hours of continuous running: it should be noted that the presence of the catalyst obtained as described above comprising silica (SiO$_2$) as binder, allows a greater duration of the second dehydration reaction (Part II) with respect to that of Example 3 in which neither said first catalytic bed comprising silica (SiO$_2$) was used, nor the catalyst comprising silica (SiO$_2$) as binder.

EXAMPLE 5

Preparation of 1,3-butadiene (1,3-BDE) by means of two dehydration reactions carried out in series starting from a mixture of 1,3-butanediol (1,3-BDO)

Example 5 was carried out under the same operating conditions described above for Example 4, with the exception that:

in Part II, a quantity of ammonium hydroxide (NH$_4$OH) was added so as to have an equivalent concentration of ammonia (NH$_3$) equal to 2.4% by weight with respect to the total weight of the compounds present in said mixture 3 [i.e. unsaturated alcohols (3-buten-2-ol and 2-buten-1-ol) and other compounds (C$_2$-C$_4$ alcohols, carbonyl compounds, etc.)], instead of being equal to 1.2% as indicated in Example 4.

The results obtained, only for the Part (II), are indicated in Table 7.

TABLE 7

| NH$_3$ equivalents (%) | Duration of dehydration (hours) | Conversion (%) | Selectivity (%) |
|---|---|---|---|
| 2.4 | 8 | 100$^{(2)}$ | 90$^{(2)}$ |
|  | 76 | 36$^{(1)}$ | 73$^{(1)}$ |

$^{(1)}$values referring to 1,3-BDE;
$^{(2)}$values referring to unsaturated alcohols.

The test was interrupted after 76 hours of continuous running; it should be noted that the presence of the catalyst obtained as described in Example 4 comprising silica (SiO$_2$) as binder, allows a greater duration of the second dehydration reaction (Part II), in spite of the greater quantity of equivalents of ammonia (NH$_3$) used, with respect to that of Example 3 in which neither said first catalytic bed comprising silica (SiO$_2$) was used, nor the catalyst comprising silica (SiO$_2$) as binder.

EXAMPLE 6 (comparative)

Preparation of 1,3-butadiene (1,3-BDE) by means of two dehydration reactions carried out in series starting from a mixture of 1,3-butanediol (1,3-BDO)

Example 6 was carried out under the same operating conditions described above for Example 4, with the exception that:

in Part II ammonium hydroxide (NH$_4$OH) was not used.

The results obtained, only for the Part II, are indicated in Table 8.

TABLE 8

| NH$_3$ equivalents (%) | Duration of dehydration (hours) | Conversion (%) | Selectivity (%) |
|---|---|---|---|
| 0.0 | 8 | 100$^{(2)}$ | 94$^{(2)}$ |
|  | 32 | 35$^{(1)}$ | 70$^{(1)}$ |

$^{(1)}$values referring to 1,3-BDE;
$^{(2)}$values referring to unsaturated alcohols.

The test was interrupted after only 32 hours of continuous running, when the conversion and selectivity values indicated in Table 8 had dropped well below those obtained in Example 1 and indicated in Table 2, and those obtained in Example 4 and indicated in Table 6, due to a high deactivation of the catalyst used in the second dehydration reaction (Part II).

EXAMPLE 7 (comparative)

Preparation of 1,3-butadiene (1,3-BDE) by means of two dehydration reactions carried out in series starting from a mixture of 1,3-butanediol (1,3-BDO)

Example 7 was carried out under the same operating conditions described above for Example 4, with the exception that:

in Part II, a quantity of pyridine [instead of ammonium hydroxide (NH$_4$OH)] was added so as to have an equivalent concentration of ammonia (NH$_3$) equal to 1.2% by weight with respect to the total weight of the compounds present in said mixture 3 [i.e. unsaturated alcohols (3-buten-2-ol and 2-buten-1-ol) and other compounds (C$_2$-C$_4$ alcohols, carbonyl compounds, etc.)].

After a few hours of continuous running, the total deactivation of the catalyst used for the second dehydration reaction (Part II), was registered.

EXAMPLE 8

Preparation of 1,3-butadiene (1,3-BDE) by means of two dehydration reactions carried out in series starting from a mixture of 1,3-butanediol (1,3-BDO)

Example 8 was carried out under the same operating conditions described above for Example 2, with the exception that:

in Part II, a quantity of pyrrole was added so as to have an equivalent concentration of ammonia equal to 0.01% by weight with respect to the total weight of the compounds present in said mixture 3 [i.e. unsaturated alcohols (3-buten-2-ol and 2-buten-1-ol) and other compounds (C$_2$-C$_4$ alcohols, carbonyl compounds, etc.)].

The results obtained, only for the Part (II), are indicated in Table 9.

TABLE 9

| NH$_3$ equivalents (%) | Duration of dehydration (hours) | Conversion (%) | Selectivity (%) |
|---|---|---|---|
| 0.01 | 8 | 100$^{(2)}$ | 92$^{(1)}$ |
|  | 78 | 99$^{(2)}$ | 95$^{(1)}$ |

$^{(1)}$values referring to 1,3-BDE;
$^{(2)}$values referring to unsaturated alcohols.

The test was interrupted after 78 hours of continuous running; it should be noted that the addition of pyrrole allows an increasing, in term of both duration and selectivity, of the second dehydration reaction (Part II), with respect to that of Example 2 in which pyrrole was not used. After 78 hours, in fact, the conversion is equal to 99% and the selectivity is much higher with respect to that of Example 2.

The invention claimed is:

1. A process of dehydrating at least one oxygenated compound, the process comprising:
feeding to a reactor a mixture comprising at least one oxygenated compound selected from the group consisting of a saturated alcohol and an unsaturated alcohol and at least one basic agent selected from the group consisting of ammonia and a nitrogen-containing compound which forms ammonia during the dehydration, wherein the mixture passes through a first catalytic bed and subsequently through a second catalytic bed, and wherein the first catalytic bed consists of silica and the second catalytic bed comprises at least one dehydration catalyst selected from the group consisting of cerium oxide, aluminum oxide, aluminum silicate, silica-alumina, a zeolite, lanthanum oxide, zirconium oxide, tungsten oxide, thallium oxide, magnesium oxide, and zinc oxide.

2. The process of claim 1, wherein the oxygenated compound comprises a saturated alcohol having from 1 to 25 carbon atoms.

3. The process of claim 1, wherein the oxygenated compound comprises an unsaturated alcohol having from 2 to 20 carbon atoms.

4. The process of claim 1, wherein the at least one oxygenated compound is provided in either (i) anhydrous form, or (ii) in mixture with water wherein the water is present in an amount greater than or equal to 0.005% by weight, based on a total weight of the mixture.

5. The process of claim 1, wherein the oxygenated compound is derived from a fermentation of one or more sugars obtained from biomass.

6. The process of claim 1, wherein the oxygenated compound is derived from a fermentation of one or more sugars obtained from guayule or from thistle.

7. The process of claim 1, wherein the basic agent is at least one selected from the group consisting of: ammonia in the gaseous form; ammonium hydroxide; urea; ammonium carbonate or bicarbonate; a primary, secondary or tertiary amine, aliphatic or aromatic, having a boiling point ranging from −8° C. to 250° C.; and a heterocyclic compound comprising a nitrogen atom.

8. The process of claim 1, wherein when the basic agent is ammonia, the ammonia is present in an amount of from 0.005% by weight to 4% by weight, based on a total amount of the oxygenated compound and optional organic compounds present, and alternatively when the basic agent is a nitrogen-containing compound which forms ammonia upon dehydration, the ammonia formed is present in an amount of 0.005% by weight to 4% by weight, based on a total amount of the oxygenated compound and optional organic compounds present.

9. The process of claim 1, wherein the process is performed adiabatically, isothermally, or a combination of both in a continuous reactor, which is a fixed-bed or a fluid-bed reactor.

10. The process of claim 9, wherein the reactor operates at:
a temperature ranging from 190° C. to 500° C.; and/or
a pressure ranging from 0.3 bara (bar absolute) to 3.5 bara (bar absolute).

11. The process of claim 9, wherein the oxygenated compound, optionally with water, is fed to the reactor operating at a WHSV ranging from 0.5 h$^{-1}$ to 30 h$^{-1}$.

12. A process comprising dehydrating at least one oxygenated compound, the process comprising:
feeding to a reactor a mixture comprising at least one oxygenated compound selected from the group consisting of a saturated alcohol, an unsaturated alcohol, and a diol and at least one basic agent that is an inorganic nitrogen-containing compound which forms ammonia during the dehydration,
wherein the mixture passes through a first catalytic bed and subsequently through a second catalytic bed, and
wherein the first catalytic bed consists of silica and the second catalytic bed comprises at least one dehydration catalyst selected from the group consisting of ammonium phosphate and a metal phosphate.

13. A process comprising:
(a) dehydrating 1,3-butanediol optionally in a mixture with water to obtain a product comprising an unsaturated alcohol, in the presence of
(i) at least one dehydration catalyst selected from the group consisting of cerium oxide, aluminum oxide, aluminum silicate, silica-alumina, a zeolite, lanthanum oxide, zirconium oxide, tungsten oxide, thallium oxide, magnesium oxide, and zinc oxide;
(ii) an inorganic nitrogen-containing compound which forms ammonia during the dehydration; and
(iii) optionally silica;
(b) distilling the product to obtain the unsaturated alcohol; and
(c) dehydrating a mixture comprising a nitrogen-containing compound which forms ammonia during the dehydration and the unsaturated alcohol to produce 1,3-butadiene, in the presence of
(i') a first dehydration catalyst in a first catalyst bed, wherein the first dehydration catalyst consists of silica; and
(ii') a second dehydration catalyst in a second catalyst bed, wherein the second dehydration catalyst is selected from the group consisting of aluminum oxide, aluminum silicate, silica-alumina, a zeolite, lanthanum oxide, and zirconium oxide, wherein the mixture comprising the unsaturated alcohol passes through the first catalyst bed and subsequently through the second catalyst bed.

* * * * *